Figure 1:
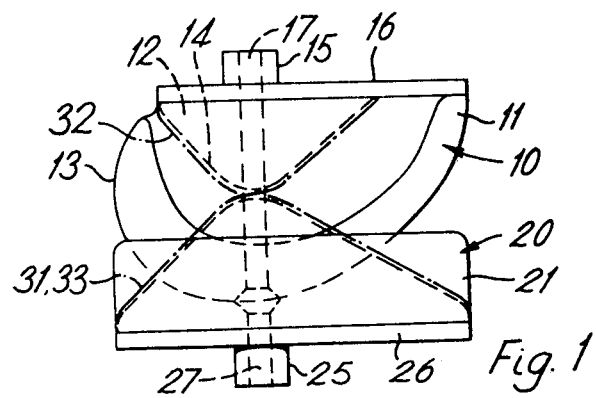

United States Patent [19]
Schofield

[11] 3,946,446
[45] Mar. 30, 1976

[54] PROSTHETIC BONE JOINT
[75] Inventor: Jack Schofield, Wirral, England
[73] Assignee: National Research Development Corporation, London, England
[22] Filed: Oct. 30, 1974
[21] Appl. No.: 519,206

[30] Foreign Application Priority Data
Oct. 31, 1973 United Kingdom............ 50594/73

[52] U.S. Cl. .................... 3/1.91; 3/1.911; 3/22; 128/92 C
[51] Int. Cl.² ................ A61F 1/24; A61F 1/04
[58] Field of Search .................. 3/1, 1.9–1.913, 3/2, 22–29; 128/92 C

[56] References Cited
UNITED STATES PATENTS
3,728,742  4/1973  Averill et al. ................ 3/1.911
FOREIGN PATENTS OR APPLICATIONS
267,810  7/1950  Switzerland............... 3/22
169,586  11/1951  Austria ..................... 3/22

Primary Examiner—Ronald L. Frinks
Attorney, Agent, or Firm—Cushman, Darby & Cushman

[57] ABSTRACT

A prosthetic bone joint device, developed initially for the knee but applicable to other joints, has first and second components each with a laterally-spaced pair of respectively convex and concave bearing surfaces, and each with a seating surface bridging the respective bearing surfaces, the seating surface being of V-shaped profile longitudinally of the component. The components are disposed with their bearing surfaces in mutual articulatory engagement, and with the V-apices of their seating surfaces in closely-spaced parallel relation, and have at least two elongate flexible linkage members extending with their opposite ends connected to respectively different ones of the components in a crossed configuration seated on the seating surfaces.

9 Claims, 3 Drawing Figures

PROSTHETIC BONE JOINT

This invention concerns prosthetic devices and more particularly prosthetic bone joint devices.

In fact the invention has been developed in relation to the knee joint and, while it is applicable to other joints, such as the ankle, it is convenient to discuss the invention in relation to knee joint devices.

Until recent times the latter devices have involved the use of a mechanical hinge interconnecting the femur and tibia for mutual pivoting movement about a fixed axis of rotation. This movement is an extremely simplified approximation to the more complicated movement during extension and flexion of the natural knee joint, and the hinge devices in question have normally involved removal of significant amounts of bone and also the ligaments involved in the movement of the natural joint.

More recently, various proposals have been made for devices having respective separate femoral and tibial components which are intended to be held in mutual bearing engagement only by the capsule of the natural joint. These devices have been associated with a wish to reduce the need for bone and ligament removal, and also to provide bearing surfaces which co-operate to simulate the movement of the natural joint more closely. However, these more recent devices have yet to be subjected to use over a sufficiently long period to properly assess their relative advantages compared to the earlier hinge-form devices.

Also, the condition of a knee joint of which the bearing function is to be replaced by a prosthesis will not always be suited to use of the more recent forms with their reliance on natural capsule elements.

Accordingly, an object of the present invention is to provide a further form of device which affords a closer approximation to the movement of the natural knee joint than does a simple hinge device, while at the same time employing a prosthetic femoral/tibial linkage to simulate the role of the natural ligaments.

To this end the invention provides a prosthetic bone joint device comprising first and second bearing components each having a pair of respectively convex and relatively concave bearing surfaces in side-by-side spaced disposition for mutual bearing engagement of the components for rotational movement at least about a direction bridging the respective bearing surfaces, and at least two elongate flexible linkage members connected at opposite ends to respectively different ones of said components in a diagonally crossed configuration extending transversely relative to said direction.

In the case of a knee joint device the convex and concave bearing surfaces preferably take the form of respective pairs of ribs and grooves having profiles which are curved both longitudinally and laterally and serve to respectively simulate the femoral and tibial condyles. This simulation is preferably taken further by the provision of lateral profiles of similar curvature for both the ribs and grooves, while the grooves have longitudinal profiles of low curvature and those of the ribs have similar low curvature towards one end but increasing curvature towards the other end. The consequence of this profiling is that the ribs can engage at their first-mentioned ends with the grooves in a relatively stable manner involving a large bearing contact area and little freedom for rotation about a direction generally orthogonal thereto, and the ribs can rotate by a combination of rolling and sliding relative to the grooves with a changing centre of rotation towards a position in which they are engaged at their other ends with the grooves in a less stable manner involving a reduced bearing contact area and some freedom for rotation about said orthogonal direction. These positions of the device correspond, or are at least compatible with, those of the natural joint at about zero flexion and when approaching full flexion. At zero flexion the natural joint is relatively stable for purposes of standing, in that it has little freedom for rotation about the longitudinal axis of the leg and it is also subject to higher bearing loading in the most frequent activity involving this position, namely, walking. As the natural joint moves towards full flexion, the capability for rotation about the longitudinal axis of the leg increases, the centre of the principal rotation progressively changes with that rotation, and the bearing loading is reduced in the normal activities, such as sitting, which involve such a position. The relationship of bearing loads in the natural joint and bearing contact area in the device are, of course, relevant to the question of wear.

Regarding the linkage members, these preferably co-operate with two seating surfaces each of generally convex V-shaped profile and respectively located between the convex and concave bearing surfaces with the V-apices extending along the direction bridging the latter areas. More particularly, it is preferred that these seating areas follow the diagonally crossed configuration of the linkage members at least in one limiting position of bearing engagement between the two bearing components.

In the case of a knee joint device this limiting position is advantageously chosen as that corresponding to zero flexion to enhance the possibility of simulating natural knee joint functions. Thus, in the limiting position in question, substantially the whole lengths of the linkage members between the bearing components seat along the seating surfaces and act against any orthogonal rotation between the bearing components. However, the bearing surfaces and linkage arrangement can be chosen so that, as the bearing components rotate in a flexion increasing manner, the linkage members lift from one pair of opposed corresponding V-arm portions of their seating surfaces (namely those portions nearer the convex bearing surface area portions of greater curvature) and rotate about the V-apices. This facilitates the possibility of orthogonal rotation between the bearing components, and also allows a relative sliding component as well as rolling to figure in the flexional rotation. Then, in a final phase of rotation towards a position of full flexion, the linkage members again seat on their seating surfaces to act against sliding while allowing orthogonal rotation between the bearing components. This overall situation is compatible with the natural joint in which orthogonal rotation capability increases with flexion, and in which initial flexion involves both sliding and rolling with subsequent termination of the sliding component.

For a fuller understanding of the present invention, a prosthetic knee joint embodiment thereof will now be described with reference to the accompanying drawings, in which:-

Figure 2:
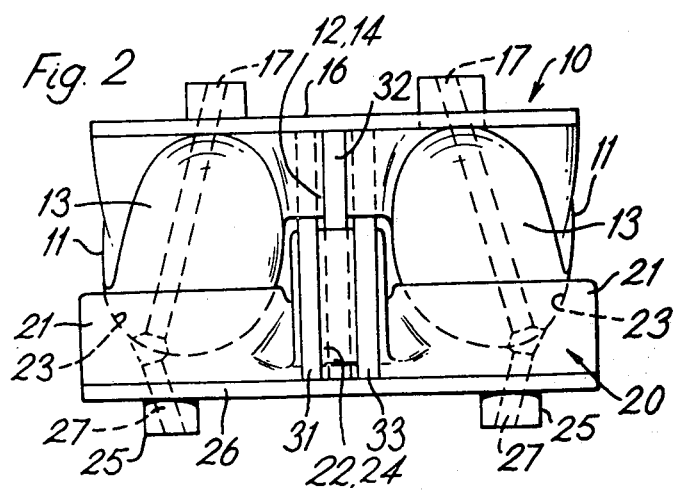
Figure 3:
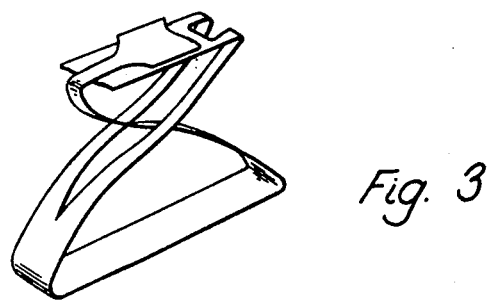

FIGS. 1 and 2 diagrammatically illustrate the relevant embodiment in side view and end elevation, respectively, and FIG. 3 illustrates a preferred form for the linkage members of such an embodiment.

The illustrated embodiment comprises a femoral component denoted generally at 10, and a tibial component similarly denoted at 20.

The femoral component comprises two similar rib portions 11 integrally connected in laterally-spaced, generally parallel disposition by a bridge portion 12. The ribs 11 define respective convex bearing surfaces 13 of which the longitudinal and lateral profiles are seen in FIGS. 1 and 2 respectively. The longitudinal profile is of a first, lower order of curvature over one end portion and increases to a second, higher order over the other end portion, while the lateral profile is of a third order of curvature which will normally be higher than said second order.

The bridge portion 12 is relieved between the rib portion surfaces 13 and itself defines a convex V-shaped seating surface 14 of which the apex extends laterally relative to the longitudinal direction of the rib portions.

The remaining feature of the femoral component 10 is the provision of a securement facility configuration remote from the bearing surfaces 13 and the seating surface 14. This facility involves the provision of two relatively short intracondylar stems 15 formed integrally with and located behind the ribs 11. These stems project through respective apertures in a plate 16 and are individually bored, as shown in broken outline at 17, to emerge in the surfaces 13 in countersunk manner. The component 10 is securable to a suitably prepared femur by passage of bone screws through the bores 17 in association with acrylic cement, and the plate 16 held against the bone can be perforated or porous to allow ingrowth of bone material.

The tibial component 20 comprises two similar grooved portions 21 integrally connected in laterally-spaced, generally parallel disposition by a bridge portion 22. The grooved portions 21 define respective concave bearing surfaces 23 of which the longitudinal and lateral profiles are seen in FIGS. 1 and 2, respectively. These profiles are of respective first and third orders of curvatures as applied to the femoral component ribs.

The bridge portion 22 is similar to that of the femoral component in defining a convex V-shaped seating surface 24 of which the apex extends laterally between the grooved portions 21. However, in the tibial component the seating surface 24 is not wholly relieved relative to the grooved portions 21: in fact, the apex of the former is at a higher level than the adjacent bearing surfaces 23.

Also, the tibial component is formed with a securement facility similar to that of the femoral component, this facility comprising two short intracondylar stems 25 behind the surfaces 23, an apertured plate 26, and bores 27 through the stems 25 and grooved portions 21.

In practice the components 10 and 20 are employed in mutual articulating relationship by engagement of their bearing surfaces 13 and 23, and this engagement and the nature of the articulating relationship involves elongate flexible linkage members extending between the components as described above. There are three such members denoted at 31, 32 and 33, and each is connected at its respective opposite ends to the components 10 and 20, by clamping between the bridge portions 12 and 22 and the respective plates 16 and 26 to extend over the seating surfaces 14 and 24. More specifically, the members 31 and 33 are connected between one longitudinal end of component 10 and the diagonally opposite longitudinal end of component 20, and the member 32 is connected between the remaining two ends of these components and is located intermediate the members 31 and 33.

In a particularly convenient arrangement the members 31, 32 and 33 can be provided by a single member formed to a shape and self-linked configuration such as shown by FIG. 3.

The disposition of the illustrated device corresponds to that of zero flexion and it is to be noted that substantially the whole lengths of the members 31, 32, 33 between the components 10, 20 are seated on the surfaces 14 and 24. However, this disposition changes with flexional movement between the components 10 and 20, this movement involving relative sliding and rolling in the longitudinal sense between the bearing surfaces 13 and 23, lifting of the linkage members from their seating surfaces, a changing capability for relative rotation between the components about a vertical axis in the plane of FIGS. 1 and 2, and a varying area of surface contact between the bearing surfaces, as described in the introductory passages above. Clearly, these features of flexional movement are not determined by the geometry of the bearing surfaces alone, but are also at least partly determined by the linkage members which additionally serve to link the components in the sense of stabilizing their relationship. In this sense the linkage members simulate the cruciate ligaments of the natural knee joint.

While the invention has been described with more particular reference to the illustrated prosthetic knee joint device, it is not intended to be limited in this way. For example, the illustrated device is symmetrical to the extent that it can be used for a left of right hand knee, but in other forms the geometry of the bearing surfaces can more closely simulate the natural condyles and require left and right hand devices. The invention is, in any case, not confined to application in a knee joint device but can, as noted earlier, be applied to an ankle joint device in which case the longitudinal geometry of the bearing surfaces can be uniform for each of a talar and tibial component. Application may also be made to those of other joints such as those of the finger and elbow. Also, while the primary interest of the invention is for application to endoprosthetic devices, application to endoprosthetic devices for artificial limbs is also possible.

I claim:
1. A prosthetic bone joint device comprising:
first and second bearing components;
and at least two flexible members linking said components;
said first and second components each having a pair of respectively convex and relatively concave bearing surfaces in side-by-side spaced disposition;
said bearing surface pairs being mutually engaged for rotational movement at least about a direction bridging the respective bearing surfaces;
said components each having a seating surface with a generally convex V-shaped profile located between the respective bearing surfaces and with the V-apex of said seating surface extending along said bridging direction;
and said flexible members seating on said seating surfaces and being connected at opposite ends to respectively different ones of said components in a diagonally crossed configuration extending trans- versely relative to said bridging direction.

2. A device according to claim 1 wherein, in at least one position of bearing engagement between said components, the V-apices of said seating surfaces are in closely adjacent parallel disposition with each of said elongate members having respective end portions thereof substantially wholly seated on diagonally-opposed sides of different ones of said seating surfaces.

3. A device according to claim 2 wherein said first component seating surface is wholly relieved between said convex bearing surfaces, and said second component seating surface projects, towards its apex, beyond said concave bearing surfaces.

4. A device according to claim 3 comprising three of said elongate members, with two of said members connected similarly between said components in laterally-spaced parallel manner and the third one of said members passing intermediate said two members.

5. A device according to claim 1 wherein at least one of said components has a plate separably engageable therewith remotely from the respective bearing surfaces to clamp portions of said elongate members therebetween.

6. A prosthetic bone joint device comprising:
first and second bearing components each having a pair of respectively convex and relatively concave bearing surfaces in side-by-side spaced disposition, said bearing surfaces being mutually engaged for rotational movement at least about a direction bridging the respective bearing surfaces;

at least two elongate flexible members connected at opposite ends to respectively different ones of said components in a diagonally crossed configuration extending transversely relative to said direction;

and at least one plate separably engaged with one of said components remotely from the respective bearing surfaces to clamp portions of said elongate members therebetween, said plate spanning said one component in said direction, and said plate and said one component having aligned bores therethrough to afford screw securement to a bone.

7. A device according to claim 6 wherein said one component has a portion thereof dimensioned to project through a bore in said plate, said one component being bored through said projecting portion.

8. A device according to claim 7 wherein said one component has two of said projecting portions associated with respective bores in said plate, said projecting portions having individual bores which open into respective ones of said one component bearing surfaces.

9. A device according to claim 6 wherein said plate is perforated or porous to afford bone in-growth.

* * * * *